United States Patent [19]

Saito et al.

[11] 4,190,653
[45] Feb. 26, 1980

[54] PESTICIDALLY ACTIVE O-ETHYL-S-N-PROPYL-O-2,2,2-TRIHALO-ETHYL-PHOSPHORO(THIONO)THIO-LATES

[75] Inventors: Junichi Saito, Tokyo; Akio Kudamatsu, Kanagawa; Toyohiko Kume; Shinichi Tsuboi, both of Tokyo, all of Japan

[73] Assignee: Nihon Takushu Noyaku Seizo K.K., Tokyo, Japan

[21] Appl. No.: 816,980

[22] Filed: Jul. 19, 1977

[30] Foreign Application Priority Data

Jul. 27, 1976 [JP] Japan .................. 51/88639

[51] Int. Cl.² .................. A01N 9/36; C07F 9/165
[52] U.S. Cl. .................. 424/224; 260/963; 260/955
[58] Field of Search .................. 260/955, 963; 424/224

[56] References Cited

U.S. PATENT DOCUMENTS

| | | | |
|---|---|---|---|
| 3,184,377 | 5/1965 | Hensel et al. | 260/963 |
| 3,798,293 | 3/1974 | Kishino et al. | 260/955 X |
| 3,839,509 | 10/1974 | Drabek et al. | 260/955 X |
| 3,845,171 | 10/1974 | Beriger | 260/940 |
| 3,892,823 | 7/1975 | Maurer et al. | 260/940 |
| 3,904,710 | 9/1975 | Oswald et al. | 260/949 |
| 3,933,947 | 1/1976 | Kishino et al. | 260/949 |

FOREIGN PATENT DOCUMENTS

| | | | |
|---|---|---|---|
| 107581 | 8/1974 | German Democratic Rep. | 260/963 |
| 48-18806 | 6/1973 | Japan | 424/225 |
| 183751 | 8/1966 | U.S.S.R. | 424/225 |

OTHER PUBLICATIONS

Wertheim, "Textbook of Organic Chemistry", 2nd Edition, 1945, p. 84.

*Primary Examiner*—Anton H. Sutto
*Attorney, Agent, or Firm*—Sprung, Felfe, Horn, Lynch & Kramer

[57] ABSTRACT

O-Ethyl-S-n-propyl-O-2,2,2-trihaloethylphosphoro (thiono) thiolates of the formula

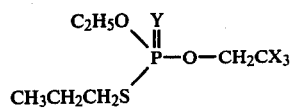

wherein Y is an oxygen atom or a sulfur atom, and X is a halogen atom.

9 Claims, No Drawings

PESTICIDALLY ACTIVE O-ETHYL-S-N-PROPYL-O-2,2,2-TRIHALOETHYL-PHOSPHORO(THIONO)THIOLATES

The present invention relates to and has for its objects the provision of particular new O-ethyl-S-n-propyl-O-2,2,2-trihaloethyl-phosphoro-(thiono) thiolates which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

The invention of Japanese Laid-Open Patent Publication No. 142516/1975 relates to a method of producing a broad range of compounds expressed by the general formula:

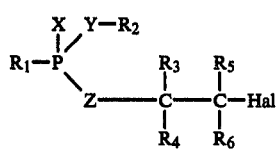

wherein
$R_1$ is a straight or branched chain $C_{1-8}$ alkyl, alkyl mercapto or alkoxy group;
$R_2$ is an alkyl group with 1 to 8 carbon atoms which may be optionally substituted by chlorine:
X is an oxygen atom;
Y and Z are each an oxygen or sulfur atom;
$R_3$ and/or $R_5$ are each hydrogen, halogen atom or other radicals; and
$R_4$ and $R_6$ are each hydrogen, or halogen or other radicals. The specification of this publication states that these compounds can be used as plasticizers and fire retardants for plastics. However, it does not suggest such compounds have insecticidal, acaricidal and nematocidal activities.

As some pests have developed resistance to several of the usually used chemicals, there is an urgent demand for the successful development of new agricultural chemicals which possess selective toxicity as between to warm-blooded animals and pests and which further work effectively against those pests which have gained resistance to earlier chemicals.

The present invention provides new compounds which have unique strong insecticidal, nematocidal and acaricidal activities, compared with analogous compounds, a broad range of pest controlling effect and an excellent activity particularly against insecticides and mites that have already gained resistance to various organic phosphate chemicals.

The present invention provides O-ethyl-S-n-propyl-O-2,2,2-trihaloethylphosphorothiolates (or thionothiolates) which are expressed by the general formula:

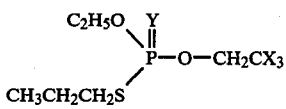

wherein
Y is an oxygen atom or a sulfur atom, and
X is a halogen atom.

It has surprisingly been found that the particular O-ethyl-S-n-propylthio (or dithio)phosphates of the present invention have unique insecticidal, acaricidal and nematocidal effects which could not be expected at all from the effects of analogous compounds.

The active compounds of the invention are relatively not at all toxic to plants and their effects are sure. Their pesticidal efforts are rapid. Hence, they can be used as agricultural chemicals for the control and extermination of a wide variety of pests such as sucking insects, biting insects, acarina and nematoda.

The compounds of the invention possessing superior insecticidal, acaricidal and nematocidal activities, can be effectively used for controlling a wide range of pests, harmful sucking insects and biting insects, other phytoparasites, grain pests and pests hazardous to man's health.

As such pests can be mentioned COLEOPTERA, for example:

*Collosobruchus chinesis,*
*Sitophilus zeamais,*
*Triobolium castaneum,*
*Epilachna vigintioctomaculata,*
*Agriotes fuscicollis* and
*Anomala rufocuprea;*

LEPIDOPTERA, for example:

*Lymantria dispar,*
*Malacosoma neustria,*
*Pieris rapae,*
*Spodsptera litura,*
*Chilo suppressalis,*
*Adoxophyes orana* and
*Ephestia cautella;*

HEMIPTERA, for example:

*Nephotettix cincticeps,*
*Nilaparvata lugens,*
*Pseudococcus comstocki,*
*Unaspis yanonensis,*
*Myzus persicae,*
*Aphis pomi* and
*Rhopalosiphum pseudobrassicae;*

ORTHOPTERA, for example:

*Blatella germanica,*
*Periplaneta americana* and
*Gryllotalpa africana;*

ISOPTERA, for example:

*Musca domestica vicina,*
*Aedes aegypti,*
*Hylemia platura,*
*Culex pipiens,*
*Anopheles sinensis* and
*Culex tritaeniorhynchus.*

As acarids, for instance, can be mentioned:

*Tetranychus telarius,*
*Panonychus citri* and
*Aculus pelekassi.*

As nematoda, for instance, mention can be made of:

*Meloidogyne incognita acrita,*
*Aphelenchoides besseyi* and
*Heterodera glycines.*

In the field of veterinary medicine the new compounds of the invention can be used effectively against various injurious animal parasites (endo- and ecto-parasites), for instance, spiders, insects and worms.

The invention also provides processes for the preparation of a phosphorothiolate (or thionothiolate) of formula (1) in which (a) a thio- (or dithio-)phosphoryl halide of the general formula:

$$\begin{array}{c} C_2H_5O \\ \diagdown \parallel \\ P-Hal \\ \diagup \\ CH_3CH_2CH_2S \end{array} \quad (II)$$

(wherein Y has the meaning given above and Hal represents a halogen atom)
is reacted with a trihaloethanol of the general formula:

$$M-OCH_2CX_3 \quad (III)$$

(wherein X has the meaning given above and M represents a hydrogen atom or an alkali metal atom).
or a salt thereof: or (b) in the case in which Y represents an oxygen atom, a phosphite of the general formula:

$$\begin{array}{c} C_2H_5O \\ \diagdown \\ P-OH \\ \diagup \\ X_3CCH_2O \end{array} \quad (IV)$$

(wherein X has the meaning given above),
is reacted with 1-propanesulfenyl chloride of the formula:

$$CH_3CH_2CH_2SCl \quad (V)$$

By way of illustration of such processes,

Process (a)

$$\begin{array}{c} C_2H_5O \quad Y \\ \diagdown \parallel \\ P-Hal + M-OCH_2CX_3 \longrightarrow \\ \diagup \\ CH_3CH_2CH_2S \end{array}$$

(II) (III)

$$\begin{array}{c} C_2H_5O \quad Y \\ \diagdown \parallel \\ P-OCH_2CX_3 + M\ Hal \\ \diagup \\ CH_3CH_2CH_2S \end{array}$$

(I)

(wherein Y, X, Hal and M have the same meanings as defined above).

In the foregoing general formula,
Y represents an oxygen atom or a sulfur atom;
X specifically represents halogen atoms such as fluoro, chloro, bromo and iodo;

Hal indicates a halogen atom which may be any of these mentioned, preferably a chlorine atom;
M represents a hydrogen atom or an alkali metal atom such as sodium or potassium.

Thio- (or dithio-) phosphoryl halides of formula (II) include, for instance,

O-ethyl-S-n-propylphosphorochloride thioate,
O-ethyl-S-n-propylphosphorochloride dithioate and bromides corresponding to these chlorides.

Trihaloethanols of general formula (II) or salts thereof include 2,2,2-trifluoroethanol,
2,2,2-trichloroethanol,
2,2,2-tribromoethanol or
sodium or potassium salts thereof.

The above process (a) is illustrated specifically by the following formula scheme:

$$\begin{array}{c} C_2H_5O \quad O \\ \diagdown \parallel \\ P-Cl + HOCH_2CBr_3 \\ \diagup \\ CH_3CH_2CH_2S \end{array}$$

$$\xrightarrow{(C_2H_5)_3N} \begin{array}{c} C_2H_5O \quad O \\ \diagdown \parallel \\ P-OCH_2CBr_3 + HCl.N(C_2H_5)_3 \\ \diagup \\ CH_3CH_2CH_2S \end{array}$$

The process may be carried out using solvents or diluents. For this purpose there can be used all inert solvents and diluents.

As such solvents or diluents can be named water; aliphatic, alicyclic and aromatic hydrocarbons which may be optionally chlorinated, for instance hexane, cyclohexane, petroleum ether, ligroin, benzene, toluene, xylene, methylene chloride, chloroform, carbon tetrachloride, ethylene chloride, trichloroethylene and chlorobenzene; ethers, for instance diethyl ether, methyl ethyl ether, di-iso-propyl ether, dibutyl ether, propylene oxide, dioxane and tetrahydrofuran; ketones, for instance acetone, methyl ethyl ketone, methyl-iso-propyl ketone and methyl-iso-butyl ketone; nitriles for instance acetonitrile, propionitrile, and acrylonitrile; alcohols; for instance methanol, ethanol, isopropanol, butanol and ethylene glycol; esters, for instance ethyl acetate and amyl acetate; acid amides, for instance dimethylformamide and dimethylacetamide; sulfones and sulfoxides, for instance dimethyl sulfoxide and sulfolane; and bases, for instance pyridine.

The reaction of the process can be effected in the presence of an acid binder. As acid binders can be mentioned hydroxides, carbonates, bicarbonates and alcoholates of alkali metals which are generally used as acid binders and tertiary amines, for instance triethylamine, diethylaniline, pyridine.

The reaction, instead of being effected in the presence of an acid binder, can afford high purity products in high yields by reacting diphosphate monochlorides with salts of trihaloethanols, preferably with the corresponding alkali metal salts of trihaloethanol.

The reaction can be carried out within a wide range of temperatures. Generally, it is done at temperatures from −20° C. to the boiling point of the mixture, and preferably from 0° to 100° C.

Although the reaction is preferably carried out under atmospheric pressure, it is possible to operate under elevated or reduced pressures.

Process (b)

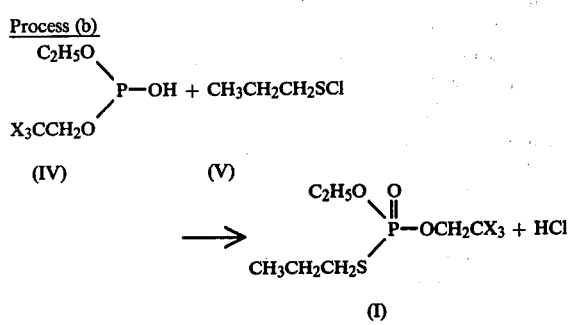

(X is the same as defined previously).

Phosphites of the foregoing general formula (IV) specifically include, for example, O-ethyl-O-2,2,2-trifluoroethylphosphite,
O-ethyl-O-2,2,2-trichloroethylphosphite and
O-ethyl-O-2,2,2-tribromoethylphosphite.

1-Propanesulfenyl chloride used in the above reaction can be readily prepared by the usual method of reacting sulfuryl chloride with dipropyl disulfide.

The above method is illustrated specifically by the following typical example.

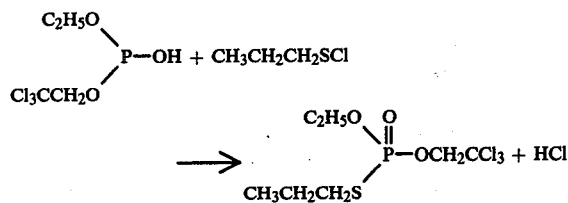

In carrying out process (b), the same type of inert solvent or diluent as mentioned already for process (a) may be used.

Process (b) can be carried out within a wide range of temperatures. Generally, the reaction is carried out at temperatures from $-20°$ C. to the boiling point of the mixture, and preferably from $0°$ to $100°$ C.

Although the reaction is preferably effected under atmospheric pressure, it is possible also to operate under elevated or reduced pressures.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, wettable powders, tablets, fumigants, aerosols, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as dichlorodifluoromethane and trichlorofluoromethane; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl ar polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides, or fungicides, bactericides, rodenticides, herbicides, fertilizers, growth-regulating agents, miticides, antiviral agents, attractants (e.g. organophosphate compounds, carbamate compounds, dithio (or thiol) carbamate compounds, organochlorine compounds, dinitro compounds, organosulfur or metallic compounds, antibiotics, substituted diphenyl ether compounds, urea compounds, triazine compounds, etc.) if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20% preferably 0.005–10% by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surfaceactive agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 3 to 1000 g/hectare, preferably 30 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combatting or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, misting, atomizing, vaporizing, scattering, dusting, watering, squirting, mixing, sprinkling, gassing, irrigating, pouring, fumigating, dressing, encrusting, coating, banding, covering, dipping, baiting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

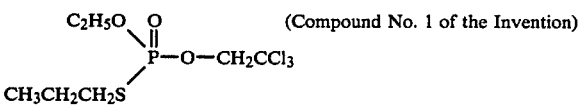

(Compound No. 1 of the Invention)

To a mixture of 6 grams of 2,2,2-trichloroethanol and 50 ml of toluene and 4.1 grams of triethylamine were added dropwise 8.75 grams of O-ethyl-S-n-propylphosphorochloride thioate under stirring at 0° to 5° C. The mixture was further stirred for two hours at 20° to 25° C. and for three hours at 60° to 70° C. after which it was cooled to room temperature followed by washing the resultant reaction mixture with 1% conc. hydrochloric acid and 2% conc. sodium hydroxide and water. The toluene-soluble mixture was dehydrated with anhydrous sodium sulfate, and the residue obtained after distilling off toluene was distilled under reduced pressure to yield the desired O-ethyl-S-n-propyl-O-2,2,2-trichloroethylphosphorothiolate in an amount of 7.6 grams.

b.p. 126°–127° C./0.3 mmHg; $n_D^{20}$ 1.4920

Typical examples of the compounds of the invention that were prepared substantially in the same way as described above are shown in Table 1.

Table 1

$$\begin{array}{c} C_2H_5O \\ \diagdown \\ CH_3CH_2CH_2S \end{array} \overset{Y}{\underset{\diagup}{P}} - OCH_2CX_3$$

| Compound No. | Y | X  | Physical Constants                              |
|--------------|---|----|-------------------------------------------------|
| 2            | S | F  | b.p. 60–61° C./0.2 mmHg  $n_D^{20}$ 1.4586      |
| 3            | O | F  | b.p. 79–81° C./0.8 mmHg  $n_D^{20}$ 1.4176      |
| 4            | S | Cl |                          $n_D^{20}$ 1.5296     |
| 5            | O | Br |                          $n_D^{20}$ 1.5320     |

EXAMPLE 2

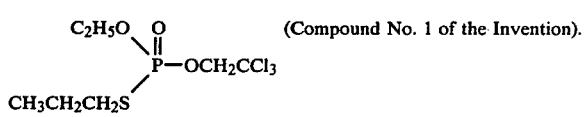

(Compound No. 1 of the Invention).

7.5 grams of di-n-propyl disulfide were dissolved in 50 ml of dichloromethane, and 6.7 grams of sulfuryl chloride was added dropwise under stirring while the temperature was being maintained below 0° C. The mixture was left standing for two hours at room temperature. While maintaining the temperature at 0° to 5° C., 24.1 grams of O-ethyl-O-2,2,2-trichloroethylphosphite were added dropwise to the mixture with stirring. The resultant reaction mixture was stirred for two hours at room temperature to complete the reaction. After the reaction, dichloromethane was removed by distillation. The residue was dissolved in benzene, washed with water, sodium hydroxide of 1% concentration and with water, and dehydrated with anhydrous sodium sulfate. Distilling off benzene from the product yielded 25.2 grams of O-ethyl-S-n-propyl-O-2,2,2-trichloroethylphosphorothiolate.

EXAMPLE 3 (Wettable Powder)

15 parts of Compound No. 1 of the invention, 80 parts of a 1:5 by weight mixture of diatomaceous earth and kaolin and 5 parts of polyoxyethylene alkyl phenyl ether were milled and mixed together to make a wettable powder. It was diluted with water and sprayed for application to insects, acarids and nematodes and/or their habitats.

EXAMPLE 4 (Emulsifiable Concentrate)

30 parts of Compound No. 3 of the invention, 30 parts of xylene, 30 parts of methyl naphthalene and 10 parts of polyoxyethylene alkyl phenyl ether were mixed and stirred together to make an emulsifiable concentrate.

The product was diluted with water and sprayed on insects, acarids and nematodes and/or their habitats.

EXAMPLE 5 (Dust)

2 parts of Compound No. 2 of the invention and 98 parts of a 1:3 by weight mixture of talc and clay were milled and mixed together to prepare a dust. The product was dusted on to insects, acarids and nematodes and/or their habitats.

EXAMPLE 6 (Dust)

1.5 parts of Compound No. 3 of the invention, 0.5 part of isopropyl hydrogen phosphate (PAP) and 98 parts of a mixture of talc and clay were milled and mixed together. The dust obtained was applied to insects, acarids and nematodes and/or their habitats.

EXAMPLE 7 (Granules)

To a mixture consisting of 10 parts of Compound No. 5 of the invention, 10 parts of bentonite, 78 parts of a 1:3 by weight mixture of talc and clay and 2 parts of lignin sulfonate were added 25 parts of water, and the mixture was thoroughly blended, attenuated by means of an extrusion type pelletizing machine to make granules of 20 to 40 mesh which were dried at 40° to 50° C. The granular product thus prepared was applied to insects, acarids and nematodes and/or their habitats.

EXAMPLE 8 (Granules)

95 parts of clay particles having a particle diameter distribution of 0.2 to 2 mm were placed in a rotary mixer and exposed, while the mixer was in operation, to the spraying of 5 parts of Compound No. 1 of the invention, which were dissolved in an organic solvent, so as to be uniformly moistened with the latter and dried at 40° to 50° C. The granules thus prepared were applied to insects, acarids and nematodes and/or habitats.

EXAMPLE 9 (Oil Preparation)

0.5 part of Compound No. 4 of the invention was mixed and stirred with 20 parts of a high boiling aromatic compound and 79.5 parts of kerosene to prepare an oil preparation. The product was applied to insects, acarids and nemarodes and/or their habitats.

EXAMPLE 10

This is a test on the larvae of *Spodoptera litura*.
Preparation of the Test Chemical
Solvent: 3 parts by weight of xylene
Emulsifier used: 1 part by weight of polyoxyethylene alkyl phenyl In order to make a suitable preparation of the active compound, one part by weight of the active compound was mixed with the solvent which contained the emulsifier, and the resulting mixture was diluted with water until the desired concentration was reached.

Test Method:
Leaves of sweet potato were dipped in a given concentration of water-diluted active compound liquid and placed in 9 cm-diameter Petri dish, in which ten third instar larvae of *Spodoptera litura* were left free. The dish was kept at a constant temperature of 28° C. and the number of the dead larvae was counted after the lapse of 24 hours to calculate the kill ratio.

The results of the test thus performed are shown in Table 2.

Table 2

Results of the Test on the Larvae of *Spodoptera litura*

| Compound No. | Kill Ratio (%) Concentration of the Active Ingredient (ppm) | | | |
|---|---|---|---|---|
| | 1000 | 300 | 100 | 30 |
| 1 | 100 | 100 | 100 | |
| 2 | 100 | 100 | 100 | 100 |
| 3 | 100 | 100 | 100 | 100 |
| 4 | 100 | 100 | 100 | |
| 5 | 100 | 100 | 100 | |
| Control Compound (A) | 0 | | | |
| Control Compound (B) | 30 | 0 | | |
| Control Compound (C) | 80 | 10 | 0 | |
| Control Compound (Dipterex) | 100 | 100 | 90 | 0 |

The control compounds in this example and in the following were as follows:

Control Compound (A): 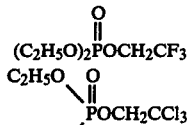

$$(C_2H_5O)_2POCH_2CF_3$$

Control Compound (B): 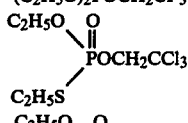

Control Compound (C): 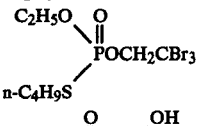

Control Compound (Dipterex): 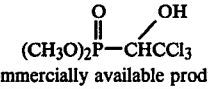

$$(CH_3O)_2P(=O)-CHCCl_3(OH)$$
(commercially available product)

EXAMPLE 11

This is a test conducted on *Callosobruchus chinensis*.
Test Method:
Filter paper was laid on a Petri dish of 9 cm diameter, and one ml of a given concentration of the waterdiluted active compound, which was prepared in the manner described in Example 10, was introduced, 20 *Callosobruchus chinensis* beetles were placed in the liquid and the Petri dish was placed in a constant temperature chamber of 28° C., and the number of dead insects was counted after a lapse of 24 hours to calculate the kill ratio.

The results are given in Table 3.

Table 3

Results of the Test on *Callosobruchus chinensis*

| Compound No. | Kill Ratio (%) Concentration of the Active Ingredient (ppm) | | |
|---|---|---|---|
| | 1000 | 100 | 10 |
| 1 | 100 | 100 | 100 |
| 2 | 100 | 100 | 100 |
| 3 | 100 | 100 | 100 |
| 4 | 100 | 100 | 100 |
| 5 | 100 | 100 | |
| Control Compound (A) | 100 | 0 | |

Table 3-continued
Results of the Test on *Callosobruchus chinensis*

| Compound No. | Kill Ratio (%) Concentration of the Active Ingredient (ppm) | | |
|---|---|---|---|
| | 1000 | 100 | 10 |
| Control Compound (B) | 100 | 0 | |

EXAMPLE 12

This is a test conducted on *Blatella germanica*.

Test Method:

Filter paper was laid in a Petri dish of 9 cm diameter, on to which was charged one ml of a given concentration of the water-diluted liquid of the active compound which was prepared in the manner described in Example 10 followed by putting 10 imagoes of *Blatella germanica* in the dish and the dish was placed in a constant temperature chamber at 28° C. After the lapse of 24 hours the number of the dead imagoes was counted to calculate the kill ratio. The results are indicated in Table 4.

Table 4
Results of the Test on *Blatella germanica*

| Compound No. | Kill Ratio (%) Concentration of the Active Ingredient (ppm) | | |
|---|---|---|---|
| | 1000 | 100 | 10 |
| 1 | 100 | 100 | 100 |
| 2 | 100 | 100 | |
| 3 | 100 | 100 | |
| 4 | 100 | 100 | |
| 5 | 100 | 100 | |
| Control Compound (A) | 0 | | |
| Control Compound (B) | 100 | 0 | |

EXAMPLE 13

This is a test conducted on houseflies (*Musca domestica vicina*).

Test Method:

Filter paper was laid on a Petri dish of 9 cm diameter, on to which was charged one ml of the water-diluted liquid of a given concentration of the active compound, prepared in the manner described in Example 10. Ten imagoes of the organophosphate-resistant *Musca domestica vicinae* were put in the dish, and the dish placed in a constant temperature chamber at 28° C. The number of the killed imagoes were counted after the lapse of 24 hours to calculate the kill ratio.

The results are given in Table 5.

Table 5
Results of the Test conducted on Organo-phosphate-resistant *Musca domestica vicina*

| Compound No. | Kill Ratio (%) Concentration of the Active Ingredient (ppm) | | |
|---|---|---|---|
| | 1000 | 100 | 10 |
| 1 | 100 | 100 | 100 |
| 2 | 100 | 100 | |
| 3 | 100 | 100 | |
| 4 | 100 | 100 | |
| 5 | 100 | 100 | |

Table 5-continued
Results of the Test conducted on Organo-phosphate-resistant *Musca domestica vicina*

| Compound No. | Kill Ratio (%) Concentration of the Active Ingredient (ppm) | | |
|---|---|---|---|
| | 1000 | 100 | 10 |
| Control Compound (A) | 0 | | |
| Control Compound (B) | 40 | 0 | |
| Control Compound (C) | 100 | 0 | |

EXAMPLE 14

This is a test conducted on *Tetranychus telarius*.

Test Method:

Leaves of a kidney bean plant at the two-normal leaf-developing stage, grown in a pot of 6 cm diameter, were inoculated with 50 to 100 organo-phosphate-resistant imagoes of *Tetranychus telarius*. On the second day a water-diluted liquid of a given concentration of the active compound prepared similarly to Example 10 was applied at a rate of 40 ml per pot, which was then placed in a hothouse. After the lapse of 10 days the control effect was evaluated on a scale of the following indices.

3: 0% survival of imagoes

2: The number of surviving imagoes is smaller than 5% of the number of imagoes in the untreated pot, but is larger than zero percent.

1: The number of surviving imagoes is larger than 5% of the number in the untreated pot, but is smaller than 50%.

0: The number of surviving imagoes is larger than 50% of the number in the untreated pot.

The results are indicated in Table 6.

Table 6
Results of the Test carried on Organo-phosphate-resistant *Tetranychus telarius*

| Compound No. | Control Index Concentration of the Active Ingredient (ppm) | | |
|---|---|---|---|
| | 1000 | 300 | 100 |
| 1 | 3 | 3 | 3 |
| 2 | 3 | 3 | |
| 3 | 3 | 3 | 3 |
| 4 | 3 | 3 | 3 |
| 5 | 3 | 3 | 3 |
| Control Compound (A) | 0 | | |
| Control Compound (B) | 1 | 0 | |
| Control Compound (Fencapton) | 1 | 0 | |

(Note)
Control Compound: (Fencapton)

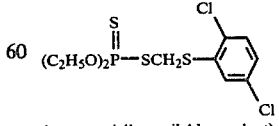

$(C_2H_5O)_2P(=S)-SCH_2S-$ (2,4-dichlorophenyl)

(commercially available product)

EXAMPLE 15

This is a test on *Meloidogyne incognita acrita*.

Preparation of the Chemicals Used for the Test.

2 parts of the active compound and 98 parts of talc were milled and mixed together.

Test Method:

The active compound prepared in the above-mentioned way was added to soil infected with *Meloidogyne incognita acrita* at concentration of 50, 25, 10 and 5 ppm, uniformly stirred and mixed and filled to a 1/5000 are-area pot. About 20 seeds of tomato (variety: Kurihara) were sown per pot and grown in a hot-house. In the fourth week the plant was withdrawn without damaging the root. Degree of damage done to 10 plants was classed and evaluated on the basis of the following standards to seek a root nodule index.

| Damage degrees | | |
|---|---|---|
| 0: | No nodule formed (complete control) | |
| 1: | nodule slightly formed | |
| 3: | nodule formed severely | |
| 4: | nodule formed most severely (corresponding to the untreated case | |
| Root nodule index = | $\dfrac{\text{(class value} \times \text{number of individual plants)}}{\text{total number of individual plants tested} \times 4}$ | × 100 |

Evaluation was made in terms of the control effect in accordance with the equation below.

Control effect =

$$\dfrac{\left(\begin{array}{c}\text{root nodule index of}\\ \text{the untreated section}\end{array}\right) \left(\begin{array}{c}\text{root nodule index}\\ \text{of the treated}\\ \text{section}\end{array}\right)}{\text{root nodule index of the untreated section}} \times 100$$

100% control effect means that the control was complete. The results are shown in Table 7.

Table 7

Results of the Test on *Meloidogyne incognita acrita*

| | Control Effect (%) | | | |
|---|---|---|---|---|
| | Concentration of the Active Ingredient (ppm) | | | |
| Compound No. | 50 | 25 | 10 | 5 |
| 1 | 100 | 100 | 100 | 100 |
| 2 | 100 | 100 | 100 | 86.6 |
| 3 | 100 | 100 | 100 | 100 |
| 4 | 100 | 100 | 100 | 80.9 |
| 5 | 100 | 100 | 100 | 100 |
| Control Compound (A) | 12.7 | 0 | | |
| Control Compound (B) | 78.8 | 0 | | |
| Control Compound (VC-13) | 100 | 98.3 | 66.4 | 7.5 |

(Note)

Control Compound: $(C_2H_5O)_2\overset{\overset{S}{\|}}{P}O\!\!-\!\!\!\left\langle\text{ }\right\rangle\!\!-\!\!Cl$ (VC-13) with Cl
(commercially available product).

It will be appreciated that the instant specification and examples are set forth by way of illustration and not limitation, and that various modifications and changes may be made without departing from the spirit and scope of the present invention.

What is claimed is:

1. An O-ethyl-S-n-propyl-O-2,2,2-trihaloethylphosphoro-(thiono)thiolate of the formula

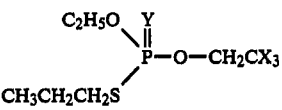

wherein
Y is oxygen or sulfur, and
X is fluorine, chlorine or bromine.

2. The compound according to claim 1 wherein the compound is O-ethyl-S-n-propyl-O-2,2,2-trichloroethylphosphoro-thiolate of the formula

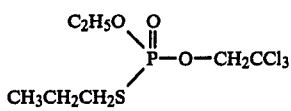

3. The compound according to claim 1 wherein the compound is O-ethyl-S-n-propyl-O-2,2,2-trifluoroethylphosphoro-thionothiolate of the formula

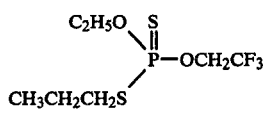

4. The compound according to claim 1 wherein the compound is O-ethyl-S-n-propyl-O-2,2,2-trifluoroethylphosphoro-thiolate of the formula

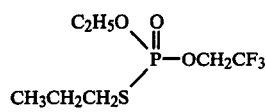

5. The compound according to claim 1 wherein the compound is O-ethyl-S-n-propyl-O-2,2,2-trichloroethylphosphoro-thionothiolate of the formula

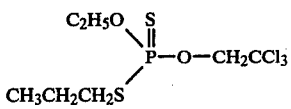

6. The compound according to claim 1 wherein the compound is O-ethyl-S-n-propyl-O-2,2,2-tribromoethylphosphoro-thiolate of the formula

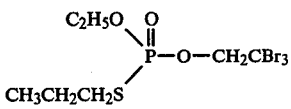

7. An insecticidal, acaricidal or nematocidal composition containing as active ingredient an insecticidally, acaricidally or nematocidally effective amount of a compound according to claim 1 in admixture with a diluent.

8. A method of combating insect, acarid or nematode pests which comprises applying to the pests or a habitat thereof an insecticidally, acaricidally or nematocidally effective amount of a compound according to claim 1 in admixture with a diluent or carrier.

9. The method according to claim 8 in which said compound is

O-ethyl-S-n-propyl-O-2,2,2-trichloroethylphosphoro-thiolate;

O-ethyl-S-n-propyl-O-2,2,2-trifluoroethylphosphoro-thionothiolate;

O-ethyl-S-n-propyl-O-2,2,2-trifluoroethylphosphoro-thiolate;

O-ethyl-S-n-propyl-O-2,2,2-trichloroethylphosphoro-thiono thiolate; or

O-ethyl-S-n-propyl-O-2,2,2-tribromoethylphosphoro-thiolate.

* * * * *